United States Patent
Wolters et al.

(10) Patent No.: US 11,905,509 B2
(45) Date of Patent: Feb. 20, 2024

(54) CELL SEPARATION APPARATUS AND METHODS OF USE

(71) Applicant: Koligo Therapeutics, Inc, New Albany, MD (US)

(72) Inventors: Rolf Wolters, Honolulu, HI (US); Jules Valenti, Seattle, WA (US); Tom Gurski, Seattle, WA (US)

(73) Assignee: Tissue Genesis International LLC, Leander, TX (US)

( * ) Notice: Subject to any disclaimer, the term of this patent is extended or adjusted under 35 U.S.C. 154(b) by 0 days.

(21) Appl. No.: 17/512,558

(22) Filed: Oct. 27, 2021

(65) Prior Publication Data

US 2022/0049209 A1    Feb. 17, 2022

Related U.S. Application Data

(60) Division of application No. 16/219,001, filed on Dec. 13, 2018, now Pat. No. 11,174,458, which is a
(Continued)

(51) Int. Cl.
*C12M 1/00* (2006.01)
*A61K 35/12* (2015.01)
(Continued)

(52) U.S. Cl.
CPC ............. *C12M 47/04* (2013.01); *A61K 35/12* (2013.01); *B04B 1/00* (2013.01); *B04B 1/02* (2013.01);
(Continued)

(58) Field of Classification Search
CPC ...... C12M 47/04; C12M 33/10; C12M 45/05; C12M 45/06; C12M 45/09; A61K 35/12; B04B 1/00; B04B 1/02
See application file for complete search history.

(56) References Cited

U.S. PATENT DOCUMENTS 1,091,989 A    3/1914    Völler et al.
1,429,320 A    9/1922    Bouillon
(Continued)

FOREIGN PATENT DOCUMENTS

CA    2859288 A1 *  6/2013    ....... A61K 39/39591
EP    3399340         11/1990
(Continued)

OTHER PUBLICATIONS

Conklin, Brian S , "A Simple Physiologic Pulsatile Perfusion System for the Study of Intact Vascular Tissue," Medical Engineering & Physics 22 (2000).
(Continued)

*Primary Examiner* — Walter D. Griffin
*Assistant Examiner* — Shuyi S. Liu
(74) *Attorney, Agent, or Firm* — Mark S. Cohen; PEARL COHEN ZEDEK LATZER BARATZ LLP

(57) ABSTRACT

Cell separation systems and methods of separating cells are disclosed. In an embodiment, a cell separation system is described that comprises a non-transitory storage device that executes a centrifugation program to separate cell volume from biologic material volume; a heating mechanism; a containment mechanism; and an assembly comprised of a single-walled centrifugation bowl. In an embodiment, methods of separating cells are disclosed whereby cells are separated by agitating a volume of biologic material and a volume digestion media to form a digested volume of biologic material; centrifuging the digested volume of biologic material; removing a portion of a resulting waste via at least one fluid outlet; isolating a different portion of the waste, and removing the concentrated cell volumes from the reservoir.

8 Claims, 11 Drawing Sheets

Related U.S. Application Data continuation-in-part of application No. 14/868,266, filed on Sep. 28, 2015, now Pat. No. 11,584,912, which is a division of application No. 11/789,188, filed on Apr. 23, 2007, now Pat. No. 9,144,583.

(51) Int. Cl.
| | | |
|---|---|---|
| *B04B 1/02* | (2006.01) | |
| *C12M 1/26* | (2006.01) | |
| *B04B 1/00* | (2006.01) | |

(52) U.S. Cl.
CPC ............ *C12M 33/10* (2013.01); *C12M 45/05* (2013.01); *C12M 45/06* (2013.01); *C12M 45/09* (2013.01)

(56) References Cited

U.S. PATENT DOCUMENTS

| | | | |
|---|---|---|---|
| 1,648,863 | A | 11/1927 | Porsi et al. |
| 1,798,579 | A | 3/1931 | Anderson |
| 1,939,087 | A | 12/1933 | Skinner |
| 1,968,600 | A | 7/1934 | Driftmeyer |
| 2,616,619 | A | 11/1952 | MacLeod |
| 3,119,398 | A | 1/1964 | Bennett et al. |
| 3,706,413 | A | 12/1972 | Blum |
| 5,035,708 | A * | 7/1991 | Alchas ............... A61L 27/34 604/35 |
| 5,051,146 | A | 9/1991 | Kapolnek et al. |
| 5,908,376 | A | 6/1999 | Macaluso et al. |
| 5,933,326 | A | 8/1999 | Lee et al. |
| 5,972,130 | A | 10/1999 | Underys et al. |
| 6,235,534 | B1 | 5/2001 | Brookes et al. |
| 7,201,848 | B2 | 4/2007 | Antwiler et al. |
| 9,144,583 | B2 | 9/2015 | Ariff et al. |
| 2002/0132341 | A1 | 9/2002 | Benedict |
| 2002/0148787 | A1 | 10/2002 | Dolecek et al. |
| 2005/0260175 | A1 | 11/2005 | Hedrick et al. |
| 2008/0014181 | A1* | 1/2008 | Ariff ............... C12M 45/05 435/308.1 |
| 2011/0111497 | A1 | 5/2011 | Tamai et al. |
| 2016/0030486 | A1 | 2/2016 | Cimino et al. |
| 2016/0252537 | A1 | 9/2016 | Murali et al. |
| 2018/0207203 | A1 | 7/2018 | Cimino et al. |

FOREIGN PATENT DOCUMENTS

| | | |
|---|---|---|
| EP | 1057534 | 12/2000 |
| GB | 2181371 | 4/1987 |
| JP | 36249857 | 3/1987 |
| JP | 52-117650 | 5/1987 |
| JP | 3-136640 | 6/1991 |
| JP | 5-505674 | 6/1994 |
| JP | H07509369 | 10/1995 |
| JP | H08-280376 A | 10/1996 |
| JP | 3-511955 | 12/1996 |
| JP | 2002-068995 A | 3/2002 |
| JP | 2004-033006 A | 3/2002 |
| JP | 2005519883 | 7/2005 |
| KR | 10-0680136 | 2/2007 |
| KR | 20070038538 | 4/2007 |
| KR | 20160006076 | 9/2016 |
| WO | WO 3312888 | 7/1993 |
| WO | WO 3501419 | 1/1995 |
| WO | WO 2006014157 | 2/2006 |
| WO | WO 2007009036 | 1/2007 |
| WO | WO 2008002094 | 1/2008 |
| WO | WO2008/133874 | 11/2008 |
| WO | WO2012/083260 A | 6/2012 |

OTHER PUBLICATIONS

Walluscheck, K.P. et al. "Improved Endothelial Cell Attachment on ePTFE Vascular Grafts Pretreated with Synthetic RGD-containing Peptides," Eur J. Vasco Endovasc. Surg. 12, 1996, pp. 321-330.
Office Action in corresponding Chinese application No. 2018801006779 dated Apr. 6, 2022.
Office Action in corresponding Chinese application No. 2018801006779 dated Dec. 20, 2022.
Office Action in corresponding Chinese application No. 2018801006779 dated Jun. 15, 2023.
Office Action in corresponding Brazilian application No. BR112021011482-3 dated Jul. 1, 2022.
Office Action in corresponding Brazilian application No. BR112021011482-3 dated Jun. 19, 2023.
Search Report for corresponding European patent No. EP 18 94 3193 dated Jul. 19, 2023.
Office action for corresponding Japanese application No. 2021-534340 dated Oct. 25, 2022.
Office action for corresponding Canadian application No. 3,123,386 dated Dec. 23, 2022.
Office action for corresponding Japanese application No. 2021-534340 dated Apr. 25, 2023.
Office action for corresponding Canadian application No. 3,123,386 dated Jun. 12, 2023.

* cited by examiner

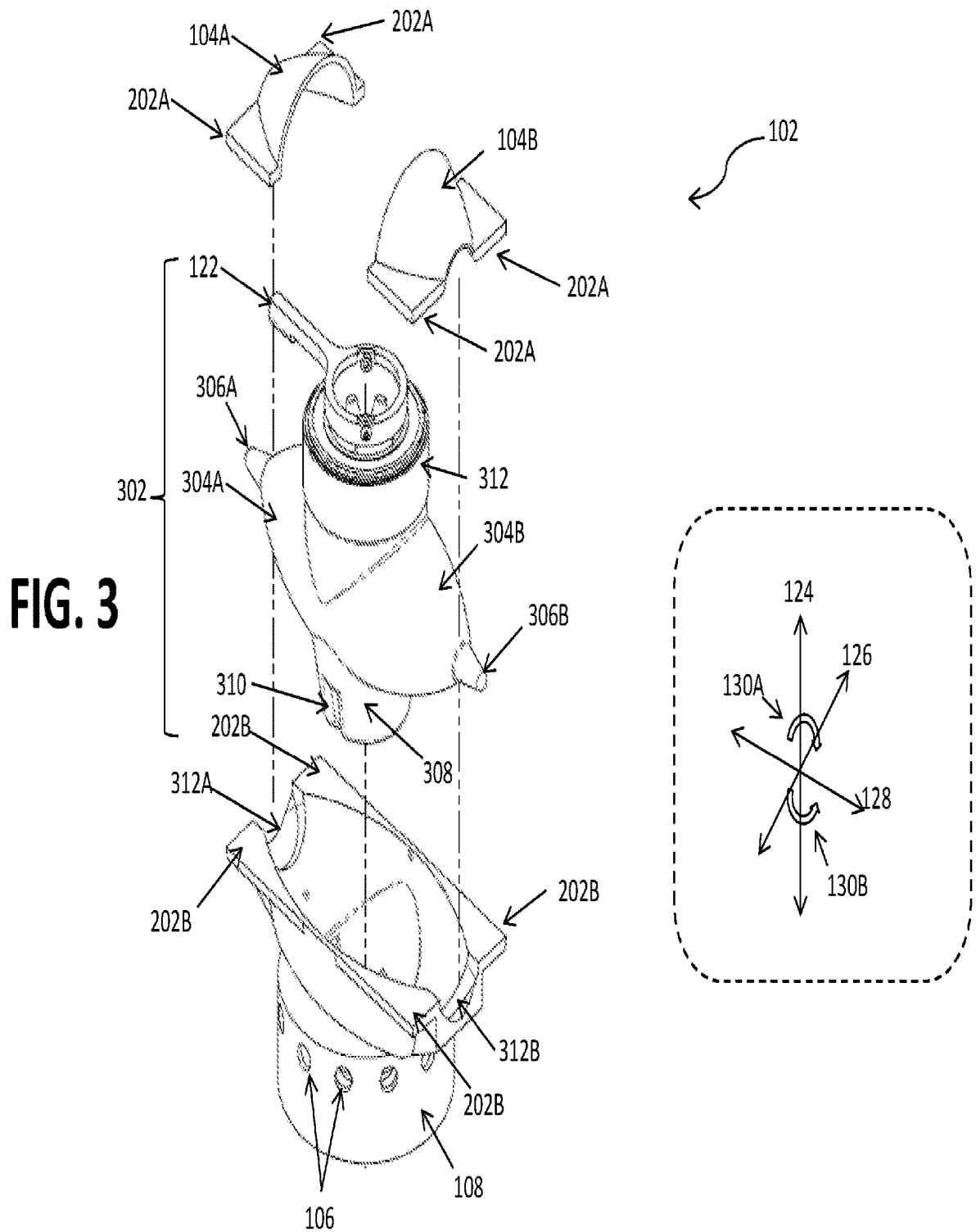

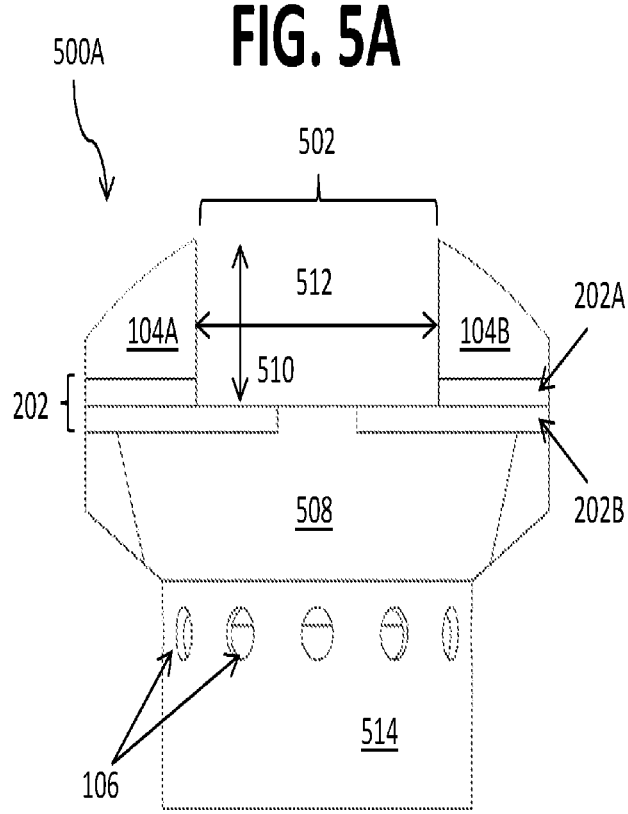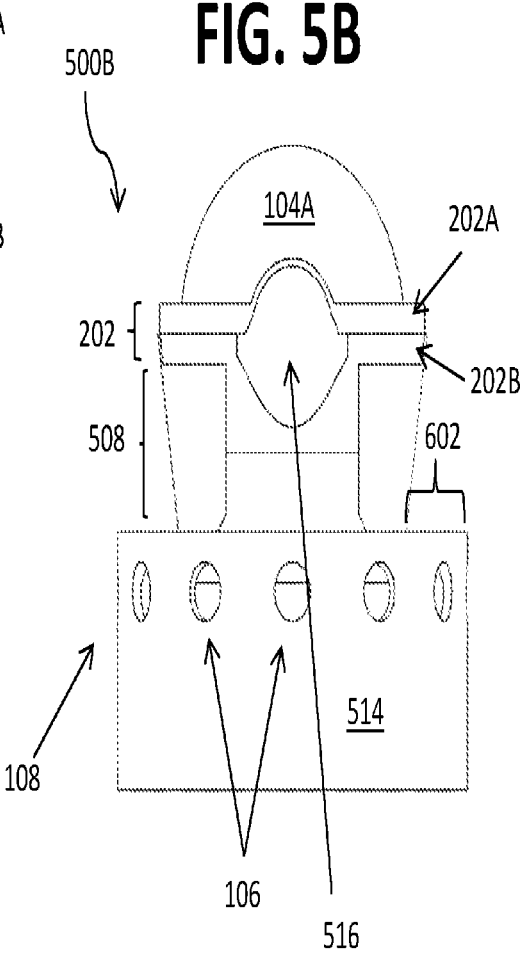

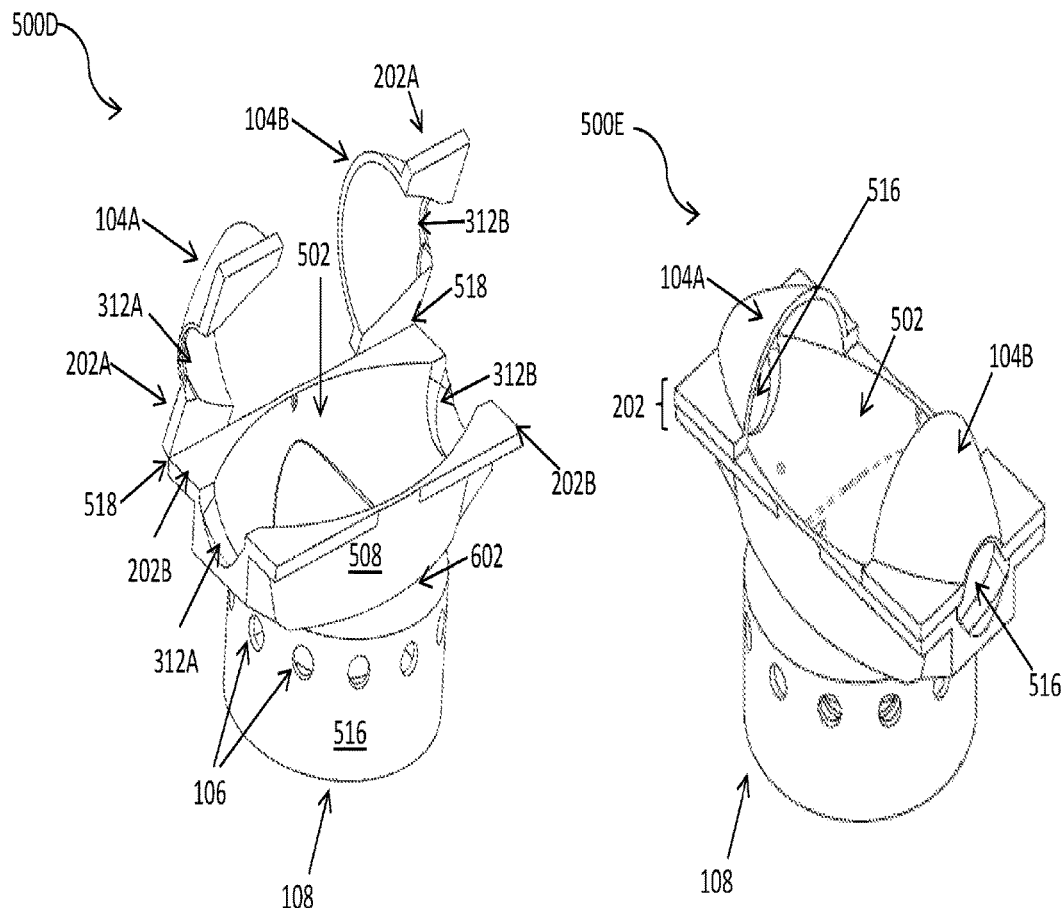

CELL SEPARATION APPARATUS AND METHODS OF USE

RELATED APPLICATION INFORMATION

This application claims priority and is a continuation-in-part of U.S. application Ser. No. 14/868,266, filed on Sep. 28, 2015 and which is a divisional of U.S. application Ser. No. 11/789,188, filed on Apr. 23, 2007, titled CELL SEPARATION APPARATUS AND METHODS OF USE, and that issued as U.S. Pat. No. 9,144,583, each of which are incorporated herein by reference in its entirety.

BACKGROUND

Cell therapy and tissue engineering is developing toward clinical applications for the repair and restoration of damaged or diseased tissues and organs. In particular, the development of tissue grafts promotes developments in surgeries, including cardiac and peripheral vascular surgery, limb tissue repair, dental applications, as well as veterinary surgeries. Grafts and other cell-based products may be formed by isolating and/or culturing cells from human or animal tissue.

Researchers have been studying synthetic grafts for over 30 years. A major challenge is providing graft materials that are biocompatible. i.e., non-thrombogenic, non-immunogenic, mechanically resistant, and have acceptable wound healing and physiological responses (e.g., vasoconstriction/relaxation responses, solute transportation ability, etc.). Furthermore, tissue graft materials should be easy to handle, store and ship, and be commercially feasible.

Vessels have two principal failure modes: mechanical and biological, caused by thrombosis within the vessel and subsequent occlusion and/or cellular ingrowth. Synthetic vessels having material properties capable of withstanding arterial pressure are commonplace, making the search for non-thrombogenic materials the prime research interest. Endothelial cells obtained from the patient have been shown to decrease the thrombogenicity of implanted vessels.

Pressure gradients involving transient high pressures have been used to deposit cells onto a permeable scaffold by a sieving action, i.e., providing a bulk flow and using a substrate or scaffold material having pores smaller than the cell population, thus capturing cells in the matrix. These captured cells have been shown to subsequently adhere to the scaffold material, but with only limited clinical applicability due to failure to fully meet the requisites for successful grafts discussed above, i.e., biocompatibility, mechanical strength, and necessary physiological properties.

Beginning in the late 1970s, endothelial cell seeding was employed experimentally to improve the patency of small diameter, polymeric vascular grafts to counteract adverse reactions. Since that time, advances have been made toward this goal, with the majority of the focus on engineering a biological or a bio-hybrid graft.

Endothelial cells are complex in that they do not merely create a single cell lining on the lumenal surface of blood vessels. Endothelial cells also release molecules that modulate coagulation, platelet aggregation, leukocyte adhesion, and vascular tone. In the absence of these cells, e.g., in the case of the lumen of an implanted synthetic polymeric vascular graft, the host reaction progresses to eventual failure. Loss of patency within the first thirty days post-implantation is due to acute thrombosis. This early stage failure is a consequence of the inherent thrombogenicity of the biomaterial's blood-contacting surface, which is non-endothelialized. To date, the only known completely non-thrombogenic material is an endothelium; any other material that comes into contact with the bloodstream is predisposed to platelet deposition and subsequent thrombosis. The long-term failure mode of small diameter polymeric vascular grafts is anastomotic hyperplasia leading to a loss of patency. The precise mechanisms behind initiation of anastomotic hyperplasia are still being defined; however, endothelial cell and smooth muscle cell dysfunctions and improper communications are likely involved.

Early workers in the field of small diameter graft development sought to promote graft endothelialization and, thereby, increase patency by transplanting a varying degree of autologous endothelial cells onto vascular grafts prior to implantation. This process has become known as endothelial cell seeding (partial coverage relying on continued cell proliferation) or cell sodding (full coverage). "Seeding" refers to a process which includes preclotting prosthetic surfaces with endothelial cells in platelet rich plasma (PRP). Sodding, by comparison, refers to a process which includes plating endothelial cells onto a pre-established PRP clot. Sodded graft surfaces are typically prepared utilizing a two-step procedure. First, PRP is clotted onto a graft, incubated for an effective period of time and then washed with culture media. Second, the PRP coated graft is plated with endothelial cells. In contrast, seeded graft surfaces are typically prepared using a one-step plating procedure, whereby endothelial cells suspended directly in PRP are plated onto a graft surface. Accordingly, in a sodded graft, endothelial cells are plated onto the surface of a PRP clot, whereas endothelial cells are plated within the PRP clot in a seeded graft.

The underlying hypothesis is fairly simple; that is, by promoting the establishment of the patient's own endothelial cells on the blood contacting surface of a vascular prosthesis, a "normal" endothelial cell lining and associated basement membrane, together known as the neointima, will form on the graft and counteract the rheologic, physiologic, and biomaterial forces working synergistically to promote graft failure. After 30 years of research in this area, including promising animal data, this simple hypothesis has not yet yielded a clinical device.

The failure modes with endothelial-seeded grafts have been identical to untreated polymeric grafts, namely thrombosis and intimal hyperplasia. The failure modes, at least partially, are linked to the lack of a functional endothelial layer, neo-intima, on the luminal surface of the graft and/or abnormal endothelial and smooth muscle cell direct and indirect communication. These failures in early human trials came despite successful demonstrations of seeded grafts developing into a cell lining development. These data show that neo-intimal formation on polymeric vascular graft lumenal surfaces in animal models occurs by endothelial cell proliferation from perianastomotic arteries, the microvessels of graft interstices, or circulating progenitor endothelial cells not strictly from the seeded cells.

A potential source for endothelial cell seeding is microvascular endothelial cells (MVEC). Williams et al. pioneered both freshly isolated and cultured human, canine, rabbit, rat, bovine and pig endothelial cells, specifically MVEC, in their laboratory to study cellular function. The source for human MVEC was aspirated tissue from cosmetic liposuction. Two separate protocols for human fat MVEC isolation were used depending on the end use of the cell population. The protocols differed in isolation complexity from a simple, operating room-compatible procedure for immediate sodding of human or animal grafts to a more elaborate procedure if the MVEC will be subsequently cultured.

A human clinical trial was undertaken to evaluate endothelial cell transplantation in patients requiring peripheral bypass. During the trial, large quantities of endothelial cells were placed directly on the lumenal surface of an ePTFE graft. To improve cell deposition, all grafts were pre-wetted in culture medium containing autologous serum. Cells were suspended in the same medium at a density of $2\times10^5$ cells/cm$^2$ graft lumenal area. This solution was held at a cross-wall, or transmural, pressure gradient of 5 psi to force cells onto the surface, a process termed "pressure sodding". After institutional approval, 11 patients were enrolled and received the experimental graft. During surgical prep, the patients underwent liposuction to remove approximately 50 grams of abdominal wall fat. The fat was processed using the aforementioned procedure and the resulting cell population was pressure sodded on the intended graft and immediately implanted. After more than 4 years of follow-up, these grafts have maintained a patency rate similar to that of saphenous vein grafts.

Pressure gradients involving transient (<1 min.) relatively high pressures (250 mmHg) have previously been used to deposit cells onto a permeable scaffold by a sieving action, i.e., providing a bulk flow and using a substrate or scaffold material having pores smaller than the cell population, thus capturing cells in the matrix. However, despite the aforementioned advances, clinical coronary applicability has been limited to date because the vessels do not maintain sufficiently cohesive non-thrombogenic surfaces; research has focused on additional maturation time in vitro.

Endothelial cells are of critical importance in establishing a non-thrombogenic cell lining. In addition, a need still exists for an efficient and reliable method for producing endothelial cell linings on a synthetic graft in an operating room setting, and the current disclosure provides a solution. It is desirable to achieve rapid cell adhesion in or on a permeable matrix, scaffold or other permeable cell substrate material in a matter of minutes or hours with an instrument that lends itself to the operating room environment, maintains a sterile barrier, is easy to use, produces consistent graft results, and is inexpensive.

LISTING OF THE FIGURES

FIG. 3 is a partial exploded view of a single-walled bowl assembly 102 according to certain embodiments of the present disclosure.

FIG. 5A is a top view of a cradle with the lid closed according to certain embodiments of the present disclosure.

FIG. 5B is a partial side view of a cradle with the lid closed according to certain embodiments of the present disclosure.

FIG. 5D is a partial isometric view of a cradle with the lid open according to certain embodiments of the present disclosure.

FIG. 5E is a partial isometric view of a cradle with the lid closed according to certain embodiments of the present disclosure.

SUMMARY

Figure 1:
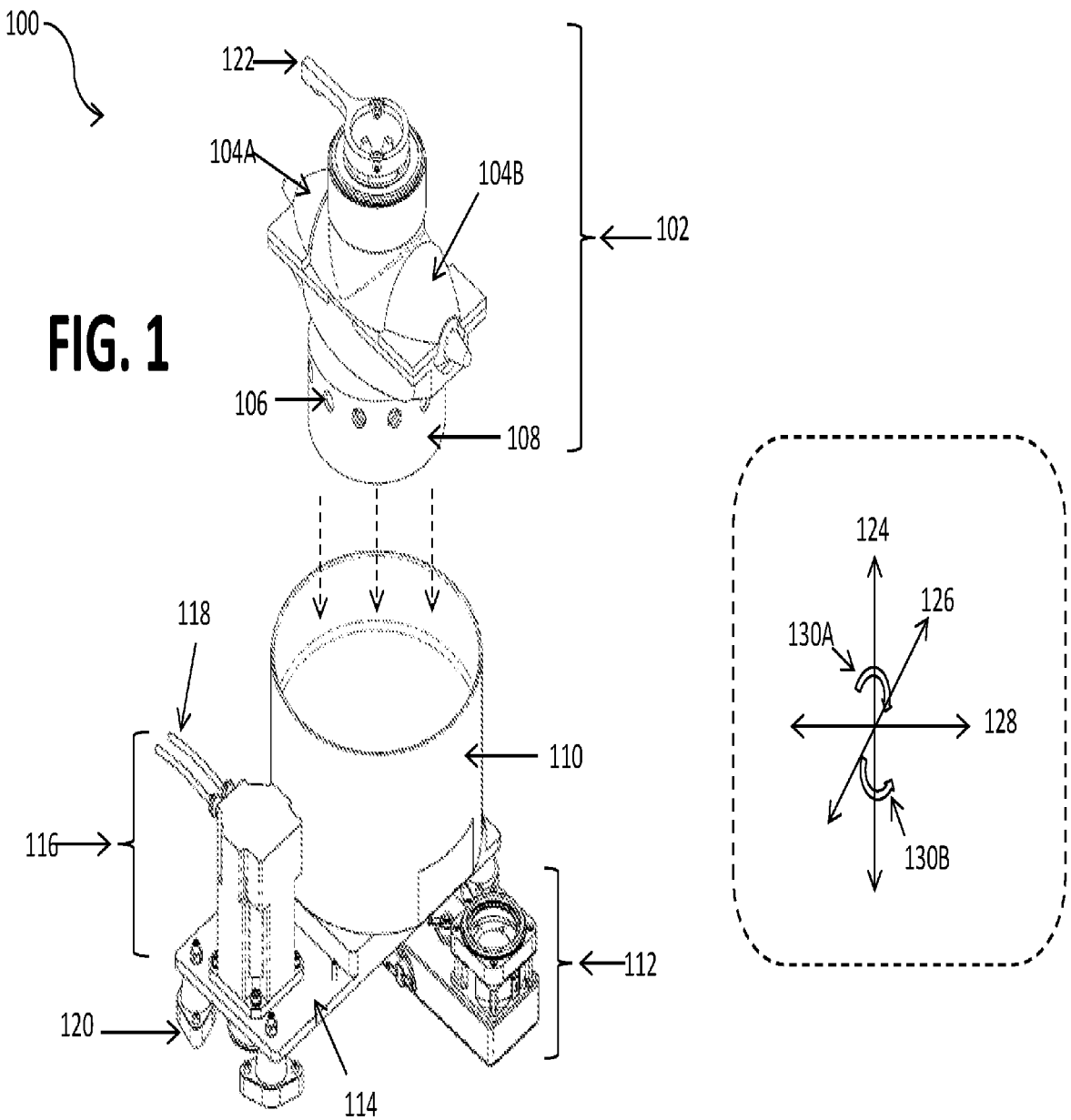
FIG. 1 is a partial isometric view of a cell separation system 100 according to certain embodiments of the present disclosure.

An embodiment of the present disclosure describes a method of separating cells, comprising agitating, in a reservoir of a cell separation system, a volume of biologic material and a volume digestion media to form a digested volume of biologic material; centrifuging the digested volume of biologic material at a force from about 500 G to about 1000 G from about 5 minutes to about 10 minutes to separate the digested volume into a plurality of concentrated cell volumes and a plurality of waste; removing a portion of the plurality of waste via at least one fluid outlet; isolating a different portion of the plurality of waste, wherein the different portion of the plurality of waste comprises waste with a larger diameter than the at least one fluid outlet and is not in contact with the concentrated cell volumes; and removing the concentrated cell volumes from the reservoir.

An embodiment of the present disclosure describes a cell separation system, comprising a non-transitory storage device comprising a plurality of logic associated with centrifugation programs, wherein execution of a centrifugation program separates a cell volume from a biologic material volume; a heating mechanism electrically coupled to a power supply; a containment mechanism in proximity of the heating mechanism; an assembly removably coupled to the containment mechanism, wherein the assembly comprises a single-walled centrifugation bowl comprising a plurality of cell concentration areas, a reservoir, and a center column comprising a plurality of fluid lines, a cradle, wherein the cradle comprises a plurality of apertures formed concentrically through the cradle, wherein the bowl is removably coupled to the cradle to enable free rotation of the bowl while coupled to the cradle, an alignment mechanism coupled to the containment mechanism and the bowl to restrict movement of the center column when the first assembly is coupled to the containment mechanism, wherein, in a first state of a centrifugation program, the assembly is configured to rotate around a central axis in a first direction and in a second direction in an alternating fashion and the heating mechanism is activated, and wherein, in a second state of a centrifugation program, the heating mechanism is deactivated and the single-walled bowl is configured to rotate in a single direction around the central axis to separate a plurality of waste from a plurality of cells.

An embodiment of the present disclosure describes a cell separation system comprising a non-transitory storage device comprising a plurality of logic associated with a plurality of different centrifugation programs, wherein, when executed by a processor; agitates, via a plurality of paddles of the system, a volume of biologic material and a volume digestion media to form a digested volume of biologic material, wherein the volume of biologic material and the volume digestion media are agitated via the plurality of paddles in a reservoir of the system; separates, via centrifugation, the digested volume of biologic material at a force from about 500 G to about 1000 G from about 5 minutes to about 10 minutes to separate the digested volume into a plurality of concentrated cell volumes and a plurality of waste; removes, based on the program, subsequent to centrifugation a portion of the plurality of waste via at least one fluid outlet; isolates a different portion of the plurality of waste, wherein the different portion of the plurality of waste comprises waste with a larger diameter than the at least one fluid outlet and is not in contact with the concentrated cell volumes; and removes the concentrated cell volumes from the reservoir.

DETAILED DESCRIPTION

Endothelial cells are used to establish non-thrombogenic cell lining within synthetic grafts. Thus, it is desirable to achieve rapid cellular adhesion in or on a permeable matrix, scaffold, or other permeable cell substrate material in a matter of minutes or hours with an instrument that lends itself to the operating room environment, maintains a sterile barrier, is easy to use, and produces consistent graft results.

Currently, there are various approaches for meeting these requirements, but with limited success: (i) the use of decellularized tissue materials; (ii) the use of a self-assembly mechanism, wherein cells are cultured on tissue culture plastic in a medium that induces extracellular matrix (ECM) synthesis; (iii) the use of synthetic biodegradable polymers, onto which cells are subsequently seeded and cultured in a simulated physiological environment; and (iv) the use of biopolymers, such as a reconstituted type I collagen gel, which is formed and compacted with tissue cells by the application of mechanical forces to simulate a physiological environment.

Embodiments of this disclosure describe systems and methods that enable the isolation of large quantities of endothelial cells from fat tissue and the rapid cell sodding of synthetic grafts, and that enable the automation and adhesion of cells in a turn-key, operating room ready instrument for the rapid sodding of the graft. Embodiments of this disclosure likely have other applications in addition to the lining of grafts for implantation.

The systems and method discussed herein are of a cell separation system that comprises a single-walled bowl that may be formed as a single piece (no seams or welds) or which may be formed as a plurality of pieces. The single-walled bowl ("bowl") may comprise various areas including a center column that houses a plurality of tubing that is used as fluid inlets, waste outlets, and extraction of the separated cells via a clean line that has not been contaminated by waste. The bowl further comprises a plurality of cell concentration areas disposed circumferentially around a central axis of the bowl such that, during centrifugation, the gravitational forces separate the cells from a biological material volume and store the cells until the waste has been collected as to not contaminate the separated cells. The bowl couples to a cradle and is coupled via a plurality of locking features and mechanisms that may be mechanical, magnetic, electrical, or a combination of mechanisms. An alignment mechanism is coupled to the bowl such that it engages with the containment mechanism in which the assembly of the bowl and the cradle is disposed.

In one example of cell separation using the cell separation system discussed herein, a plurality of logic is stored in a non-transitory storage device (memory) and comprises a plurality of centrifugation programs. Each program of the plurality of programs comprises instructions that may be based upon a plurality of factors including media type and biological material volume and/or target cell volume or target cell concentration. When executed by a processor, each program initiates cell separation through a plurality of states as discussed herein, resulting in the automated removal of the separated cells and the trapping and/or removal of waste. The programs may differ and/or overlap in various aspects, including temperatures, times, forces, and overall program length (time) from disposal of the biologic material volume and the media until the removal of the separated cell volume.

In one example of the cell separation system, a plurality of digestion media, and a plurality of biologic material (a volume) are disposed in the bowl, in particular in a reservoir of the bowl. The bowl is then agitated, rotated in each direction around the central axis to break up the biologic material volume to enable the separation during centrifugation. The agitation may be promoted by a plurality of positive features that may be referred to as paddles or fins. In one example, these features are formed integrally with the bowl, and in another example they may be removable, separate components. The bowl may be heated prior to and/or during the agitation via a heating mechanism, the heat generated by the heating mechanism causes the air in a gap between the cradle and the containment mechanism to heat up, and the plurality of apertures in the base of the cradle enable the circulation of this heated air. The bowl may be heated from about 25 C to about 45 C, and the heating mechanism may be shut off subsequent to completion of agitation such that the remainder of the cell separation occurs at room temperature (from about 20° C. to about 25° C.).

Subsequent to the agitation, centrifugation is performed. During centrifugation, the cell separation assembly of the bowl and cradle rotates freely with respect to the containment mechanism and an alignment mechanism. The centrifugation may be performed at a force from about 500 G to about 1000 G for from 5 minutes to 20 minutes, or from 1 minute to 10 minutes, or other ranges of time in various embodiments. Cells are separated from the mixture in the reservoir and are gravitationally forced into a plurality of cell concentration areas of the bowl. After the centrifugation, the speed of the bowl is reduced to 10%-30% of the average rotation force during centrifugation, and a plurality of waste materials are removed via a plurality of fluid lines. Waste that has a diameter larger than the fluid lines (fluid outlets) is trapped in a waste region and does not contact the separated cell volume. The rotation may be stopped, causing the collected cells in the cell concentration areas to slide down the sides of the bowl and into the reservoir where the cells are removed via the clean line. In other examples, a volume of media less than 10 mL or 5 mL is jet-sprayed into the cell concentration areas in order to remove any remaining cells. By using a single-walled bowl, the heat transfer may be more effective, thus increasing the efficiency of the system and reduces the cost associated with cell separation.

FIG. 1 is a partial isometric view of a cell separation system 100 according to certain embodiments of the present disclosure. The cell separation system 100 comprises an assembly 102 of a single-walled centrifugation bowl 104 coupled to a cradle 108 via a plurality of coupling mechanisms including a first 104A and a second 104B lid portion. The assembly 102 is configured such that an alignment mechanism 122 acts to stabilize the assembly 102 and allow free rotation of the assembly 102 (the bowl 302 as coupled to the cradle 108). During centrifugation, the assembly 102 spins in either direction 130A or 130B around a central axis 124, shown in a coordinate system in FIGS. 1 and 3 and referenced throughout. The coordinate system further comprises a second axis 126 that is perpendicular to the central axis 124, and a third axis 128 perpendicular to both 124 and 128. The cradle 108 is seated in and removably coupled to a containment mechanism 110, which acts to direct the heat and hot air generated by the activation of the heating unit 116. The coupling of the containment mechanism 110 to the assembly 102 creates an air gap between the two through which hot air may be circulated via an open bottom of the cradle 108 (not shown) and through the plurality of apertures 106 in the cradle 108. A hot air blower 112 also operates to circulate air in the system. In an embodiment the single walled bowl assembly 102 and associated tubing are disposable.

In an embodiment, the heating unit 116 is employed to elevate a temperature of the system 100 during at least agitation. The heating unit 116 is coupled to a base 114 comprising a plurality of feet 120 configured to prohibit movement of the base 114 and system 100 during execution of a plurality of centrifugation programs. The heating unit 116 may be wired or wireless, and, if wired via 118, may be coupled to a power source during use and/or to charge a wireless battery or batteries contained in the heating unit 116. The heating unit 116 further comprises a plurality of heating elements configured to elevate a temperature of the containment mechanism 110 and thus the assembly 102 coupled to the mechanism 110. The containment mechanism 110 may also be coupled or removably coupled to the base 114 as well.

In an embodiment, the system 100 may comprise at least one storage device (not shown) comprising a plurality of centrifugation programs and a processor, as well as a plurality of controls (not shown) activated by the execution of a centrifugation program via the processor. The storage device and/or the plurality of controls that may be located on the system 100 or located remotely and accessed via a tablet, mobile phone, wearable technology, kiosk, laptop computer, or desktop computer. Each centrifugation program may comprise a plurality of parameters employed in the centrifugation cycle, and may be selected manually or dynamically and in an automated fashion based upon inputs such as the biologic material volume used and/or the volume and/or type of digestion enzyme(s) employed.

Figure 2:
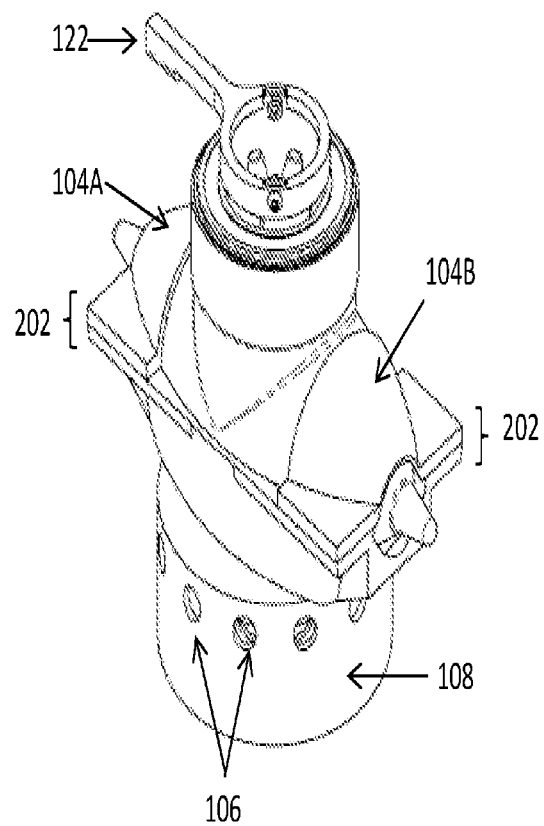
FIG. 2 is a partial isometric view of a single-walled bowl assembly 102 according to certain embodiments of the present disclosure.

FIG. 2 is a partial isometric view of a single-walled bowl assembly 102 according to certain embodiments of the present disclosure. FIG. 2 illustrates the bowl-to-cradle locking mechanism 202 that includes the first 104A and second 104B lids as well as components discussed below. The feature 202 is referred to herein as a locking mechanism 202 to generally refer to the coupling of the lid portions 104A and 104B to the cradle 108 via the "edge" features of the locking mechanism 202 that align and are removably coupled as discussed in detail in FIG. 3. In another embodiment, the locking mechanism 202 is comprised of a magnetic latch or magnetic catching mechanism removably coupled to the bowl assembly 102.

FIG. 3 is a partial exploded view 300 of a single-walled bowl assembly 102 according to certain embodiments of the present disclosure. FIG. 3 shows the first lid portion 104A and the second lid portion 104B, as well as the associated first portions 202A of the locking mechanism 202 that are removably coupled to the second portions 202B that are a part of the cradle 108. The single-walled bowl 302 is shown here, this bowl 302 may be fabricated as a single, seamless piece or as multiple pieces assembled into the bowl 302, as discussed below. The "single-wall" of the bowl is in contrast to a bowl that has at least two nested walls.

In an embodiment, the bowl 302 comprises a first shoulder 304A that couples to the first lid portion 104A and a second mating lid portion 312A, and a second shoulder 304B along a shared axis that is perpendicular to a central axis 124 and that couples to the second lid portion 104B and a second mating lid portion 312B. The lid portions 104A, 104B, the mating lid portions 312A, 312B, and the first 202A and second 202B portions of the locking mechanism 202 (formed when 202A and 202B are removably coupled via mechanical, magnetic, or other means) act to secure the bowl 302 in the cradle 108 during operation. Once secured, the assembly 102 rotates freely with respect to the containment mechanism, which does not rotate and acts at least in part to direct and circulate heated air towards the bowl 302 during agitation (and breakdown) of the biologic material volume.

In an embodiment, the bowl 302 further comprises a first 306A and a second 306B cell concentration area that each comprise smooth internal geometries and act to isolate and concentrate, via the removal of fluid and solids, the cells separated during centrifugation. A cradle mating portion 308 of the bowl 302 may extend downward into and be seated in the cradle, as discussed below. A center portion of the bowl 302 including a collar 312 houses the alignment mechanism 122 and a plurality of tubing and access points (not shown here). The alignment mechanism 122 prevents the bowl 302 and cradle 108 from spinning or rotating while interfacing with the containment mechanism 110.

In an embodiment, the bowl 302 further comprises an indentation 310 or a plurality of indentations 310 shown on the outside of the bowl 302 in FIG. 3 but formed using the wall of the bowl 302 such that an internal rib or ribs are formed by the indentation and on the interior surface of the bowl 302. This rib or ribs extend into a chamber area (not shown in FIG. 3) where the digestion occurs, and thus may be referred to as a digestion chamber of the bowl 302, and the rib or ribs act to promote digestion by agitation of the bowl 302 as discussed in the method in FIG. 6. The positive features formed by the indentations 310 on the interior of the bowl 302 may be referred to as paddles or ribs and are discussed further below.

Figure 4A:
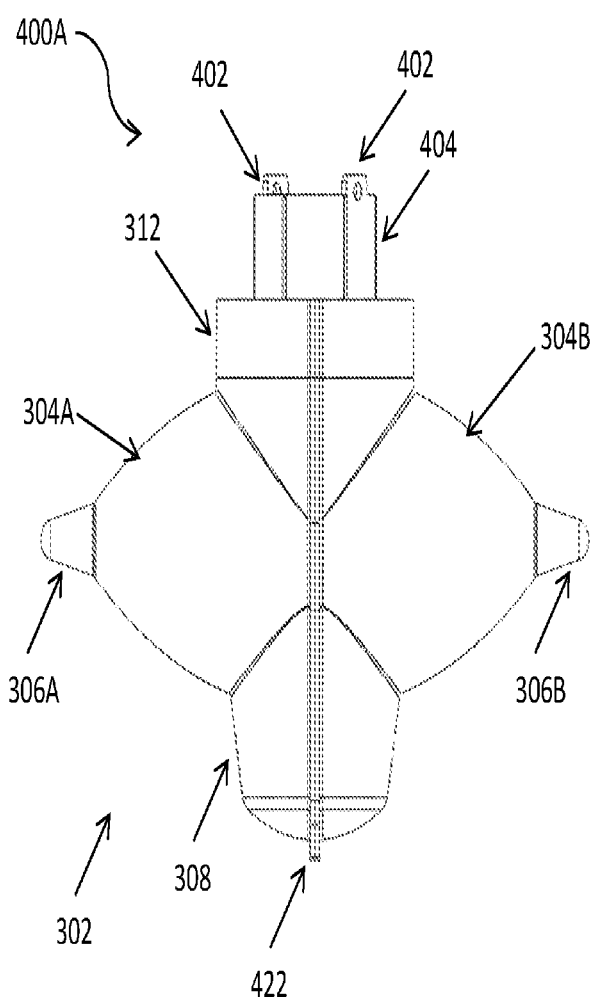
FIG. 4A is a front view of a seamed single-walled bowl according to certain embodiments of the present disclosure.

FIG. 4A is a first view 400A of a seamed single-walled bowl 302 according to certain embodiments of the present disclosure that may be referred to as a partial front view 400A. The view 400A of the bowl 302 is taken parallel to the axis 128 in FIG. 3. As shown in FIG. 4A, the bowl 302 may comprise an at least one seam 422 along a centerline of the bowl 302. Also shown in FIG. 4A are a plurality of attachment mechanisms 402 that removably couple to the alignment mechanism (122 not illustrated here) and a center column or cavity 404 that retains a plurality of tubing discussed below configured to introduce the biological material volume and clean fluids and remove waste fluids and solids.

FIG. 4A additionally illustrates the first and second shoulders 304A and 304B and the cell concentration areas 306A and 306B, all of which are formed as integral parts of the bowl 302 in an example where there is no seam 422, such as that shown in FIG. 3. The alignment mechanism 122 (FIG. 3) is removably coupled to the containment mechanism 110 and prevents the center column 404 from moving, thereby permitting the assembly 102 to spin relative to the containment mechanism.

Figure 4B:
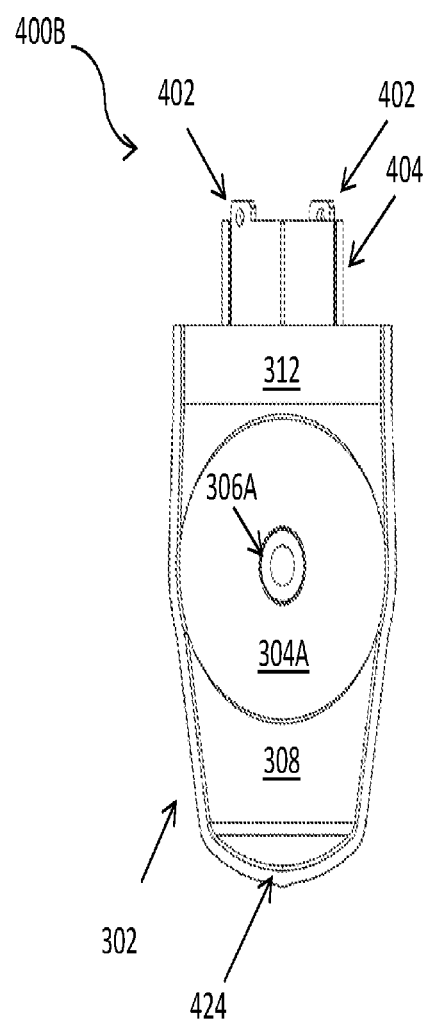
FIG. 4B is a partial side view of a single-walled bowl according to certain embodiments of the present disclosure.

FIG. 4B is a partial side view 400B of a single-walled bowl 302 according to certain embodiments of the present disclosure. FIG. 4B is a view perpendicular to the axis 128 as shown in the inset in FIG. 3. FIG. 4B shows features illustrated in FIGS. 1-4A, including the collar 312, first concentration area 306A, the plurality of attachment mechanisms 402, the center column 404, the shoulder 304A, and a rounded bottom portion 424. The rounded bottom portion 424 of the bowl 302 is seated in the cradle (not shown here) and is a smooth, continuous surface.

Figure 4C:
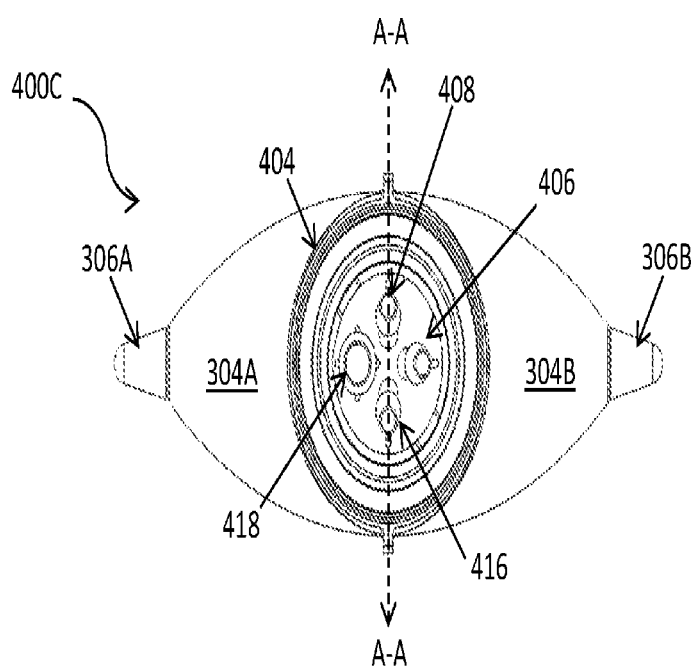
FIG. 4C is a partial top view of a single-walled bowl according to certain embodiments of the present disclosure.

FIG. 4C is a partial top view 400C of a single-walled bowl according to certain embodiments of the present disclosure. FIG. 4C is a view taken perpendicular to the axis 124 as shown in the inset in FIG. 3. FIG. 4C illustrates a plurality of fluid lines 406, 408, 416 and a waste outlet 418, discussed in detail below. A plurality of tubing and/or syringe or other collection and introduction vessels may be coupled to the entry ports of the lines 406, 408, 416, and 418, depending upon the functions of each line. In various embodiments, some fluid lines are employed to introduce biological material, some introduce media such as digestion enzymes, some may introduce other media, at least one is employed for waste removal, and at least one is a clean line used for the removal of the separated cells so that the cells are not contaminated by the waste fluid or tissue.

Figure 4D:
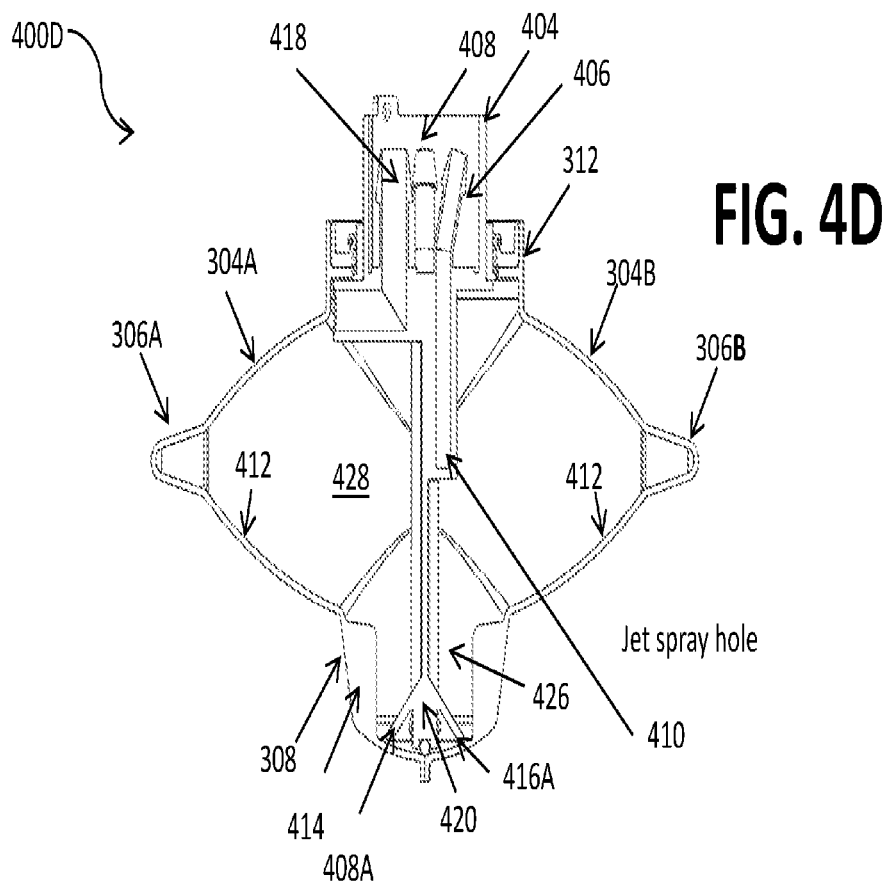
FIG. 4D is a partial cross-sectional view of a single-walled bowl taken across the bowl through the pellet concentration areas according to certain embodiments of the present disclosure.

FIG. 4D is a partial cross-sectional view 400D of a single-walled bowl taken across the bowl through the pellet concentration areas according to certain embodiments of the present disclosure. FIG. 4D is a view taken perpendicular to the 128 axis as shown in the inset in FIG. 3. FIG. 4D illustrates the bowl chamber 428, which is the interior of the bowl 302. The bowl chamber 428 comprises at least the concentration areas 306A and 306B, the reservoir 426, a waste block 420, center column 404, and a plurality of agitation paddles 414. A plurality of fluid transport tubes and ports are contained in the center column 404. These may include a jet spray inlet 406 configured as a media inlet, first 408 and second 416 fluid lines, each configured to introduce media or other fluids or biologic materials and to withdraw media or biologic materials. If one of the first 408 and second 416 lines are employed solely to introduce media, this line may be referred to as the "clean" line. That is, once either of lines 408 or 416 are used to withdraw fluids or solids from the bowl 302, that line may not be used to introduce clean media or other fluids or biologic materials to prevent contamination. Each of the lines 406, 416, and 408 (FIG. 4C and 4E) may be coupled to flexible tubing extending from a top surface of the bowl 302.

In some examples, a syringe or other sterile collection device may be coupled to one of 408 and 416, depending upon which is designated as the clean line. This sterile collection device is removably coupled to whichever line is the clean line since that line is used to remove the concentrated cells after separation. Also shown in the center column 404 is a waste outlet 418 also called a skimmer. The waste outlet 418 may have a larger diameter than the fluid lines 408 and 416 and may be able to remove larger solids. Also shown in FIG. 4D are the paddles 414 which may be formed from the indentations 310 from FIG. 3 or which may be formed separately. Two or more paddles 414 may be employed for agitation as discussed in FIG. 3. Also shown in FIG. 4D are access points 408A and 416A.

The waste block 420 is configured to isolate (trap) solids that are too large to be removed via the lines 416 and 408. By trapping solids that are too large to exit via a fluid line, these particles are prohibited from clogging the system. The smooth interior surface 412 of the bowl 302 is also shown, it is along here where the cells collected in the concentration areas 306A and 306B are released when centrifugation is stopped or slowed, the cells are retained in the reservoir 426 and removed through the clean line, which is one of 408, 416, or 406. The waste block 420 is fluidly connected to the fluid lines 408 and 416 and may be described as an inverted conical shape.

Figure 4E:
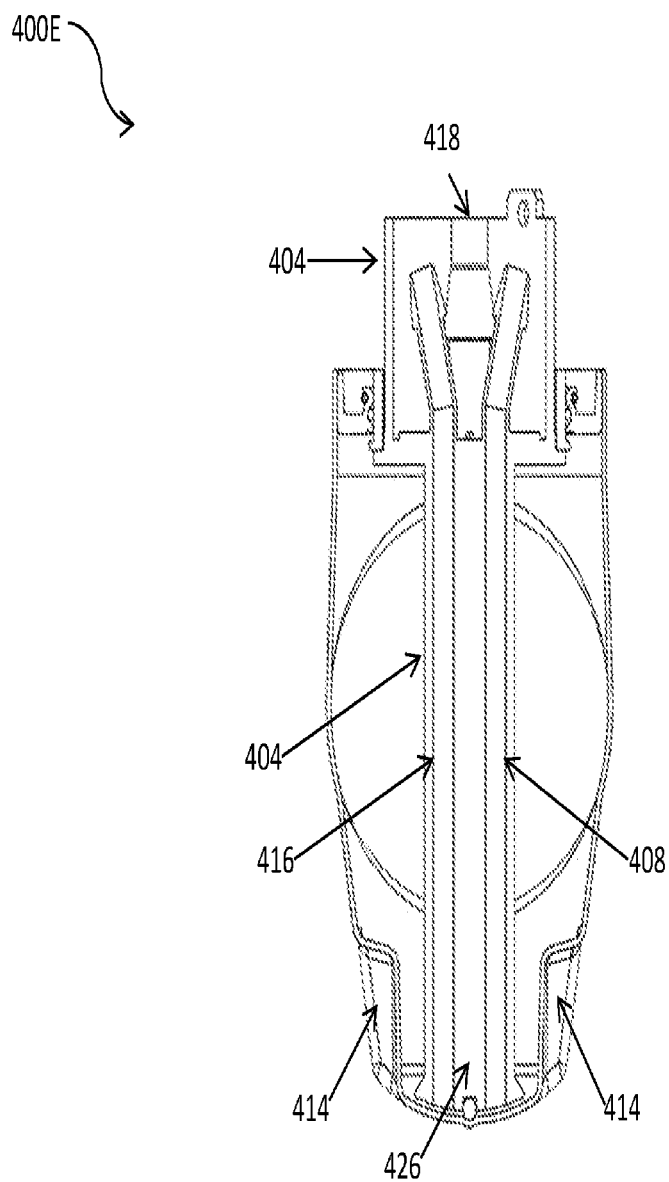
FIG. 4E is a partial cross-sectional view of a single-walled bowl taken across the bowl perpendicular through the pellet concentration areas according to certain embodiments of the present disclosure.

FIG. 4E is a partial cross-sectional view 400E of a single-walled bowl taken across the bowl perpendicular through the pellet concentration areas according to certain embodiments of the present disclosure. FIG. 4E is a view taken perpendicular to the 128 axis as shown in the inset in FIGS. 4A and 4B. FIG. 4E illustrates the fluid lines 416 and 408 that extend to the bottom of bowl chamber 428 but do not contact the interior surface of the bottom of the bowl chamber 428, such that the lines 416 and 408 introduce and/or remove materials to and/or from the reservoir 426.

FIG. 5A is a partial front view 500A of a cradle 108 with the lid closed according to certain embodiments of the present disclosure. FIG. 5A illustrates a cradle base 514 comprising the plurality of apertures 106, these apertures 106 act to release heat generated during cell separation cycles. A cradle neck 508 extends from the base 514 to the first 104A and second 104B lid portions and the locking mechanism 202. A single-walled bowl as described herein is secured to the cradle 108 via the lid portions 104A and 104B and the locking mechanism 202, and it rests in part in the recess 502 formed in the neck 508 and defined by a first dimension 512 and a second dimension 510, as well as a depth (not shown here).

Figure 5C:
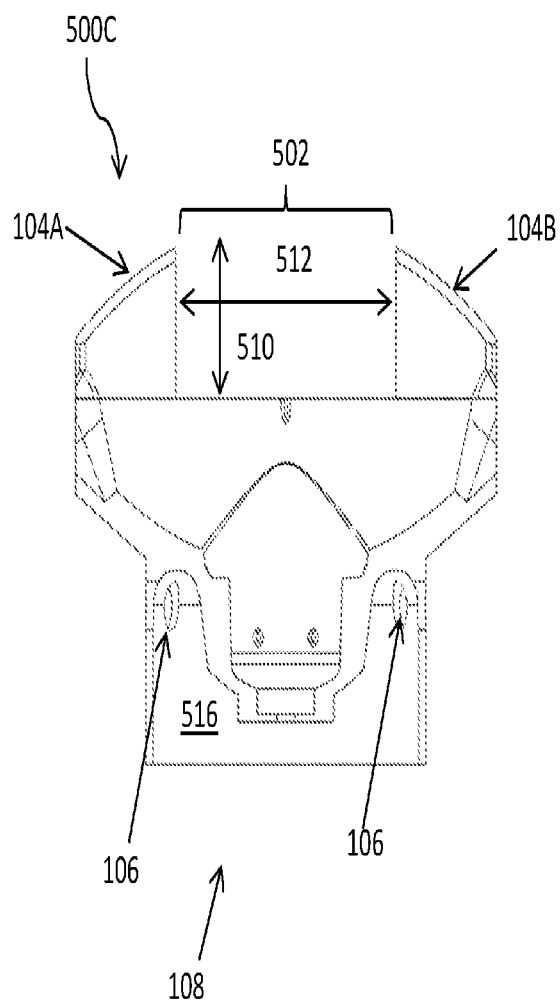
FIG. 5C is a partial front cross-section view of a cradle with the lid closed according to certain embodiments of the present disclosure.

FIG. 5B is a partial side view 500B of a cradle 108 with the lid closed according to certain embodiments of the present disclosure. FIG. 5C is a partial front cross-section view 500C of a cradle 108 with the lid closed according to certain embodiments of the present disclosure. FIGS. 5B and 5C are discussed interchangeably herein. FIG. 5B illustrates elements previously discussed as well as a cradle edge 602 which extends around the outside diameter of the base 514 and connects to the neck region 508. When the lid is closed, as is pictured in FIG. 5B, the lid portions 104A and 104B are coupled to the cradle 108 via the first portions 202A that extend from each lid 104A and 104B, respectively, and are removably coupled to the second portions 202B to form the locking mechanism 202 via mechanical, magnetic, or other means. FIG. 5B additionally shows aperture 516 that extends through the cradle 108 and is where the shoulders (304A and 304B from FIG. 3) are secured when the bowl is coupled to the cradle 108.

FIG. 5D is a partial isometric view 500D of a cradle with the lid open according to certain embodiments of the present disclosure. In FIG. 5D, the locking mechanism portions 202A of the lids 104A are partially coupled to the locking mechanism portion 202B of the cradle 108 at hinge regions 518. The aperture 516 shown in FIG. 5B is formed during lid closure by 312A, 312B, and of each of the first 104A and second 104B lid portions when the first locking mechanism portion 202A is partially coupled to the second locking mechanism portion 202B. As used herein, a "partial coupling" comprises a hinged coupling 518 as shown in FIG. 5D, and a "full coupling" comprises a closed lid as shown in at least FIGS. 5A-5C and FIG. 5E.

FIG. 5E is a partial isometric view 500E of a cradle 108 with the lid closed according to certain embodiments of the present disclosure. FIG. 5E illustrates the lid closed such that the locking mechanism 202 is engaged, which secures the bowl (not shown) in place and the aperture 516 is formed.

Figure 6:
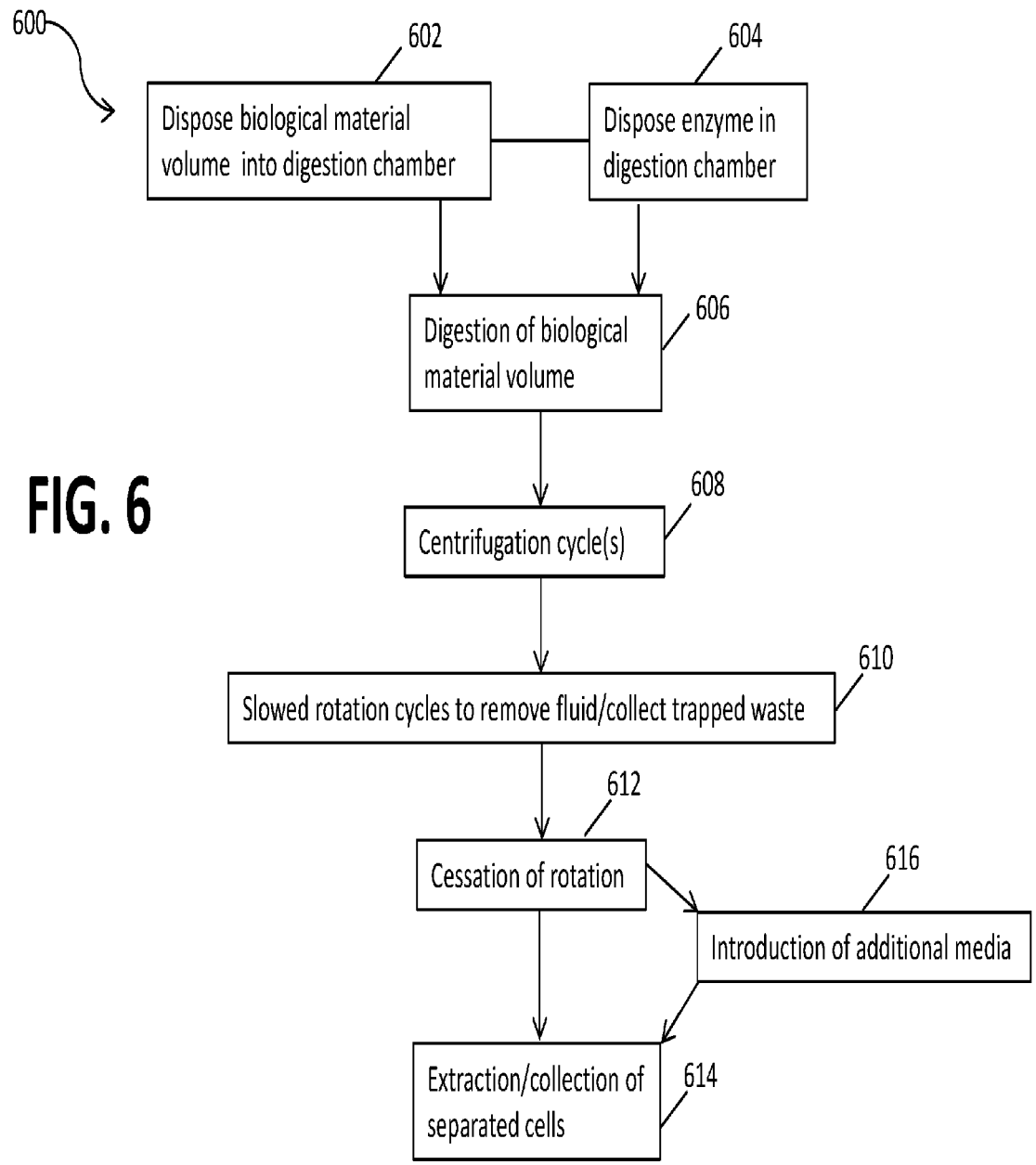
FIG. 6 is a method of separating endothelial cells from biologic material such as adipose tissue according to certain embodiments of the present disclosure.

FIG. 6 is a method of separating endothelial cells from biologic material according to certain embodiments of the present disclosure. The method 600 is an automated mechanism for the washing, separation, concentration, and removal/harvesting of viable cells such as endothelial cells. The harvested cells may be employed for grafts or otherwise employed for use in healthcare (e.g., FDA approved implantation or further processing) and/or healthcare research (trials to approve cell separation methods and cell-derivative products for use).

In an embodiment, at block 602 of the method 600, a biologic material volume is disposed in a reservoir 426 (FIG. 4D) of a single-walled bowl of a cell separation system such as the system 100 in FIG. 1. At block 604, a plurality of media and a collagenase enzyme or enzymes may be introduced into the chamber 302 in particular into the reservoir 426 via any or all of the lines 406, 408, or 416 as discussed above with respect to clean lines. The media may be fed into the system at block 604. Examples of media may be Lactated Ringers (LR), Hartmans, Water For Injection (WFI) or any other similar media. In some examples, the reservoir 426 may be pre-heated to from about 30° C. to about 40° C. prior to disposal of the biologic material volume and/or media in the chamber. In some examples, block 602 may occur prior to block 604, and in other examples, block 604 may occur prior to block 602. In still other examples, blocks 602 and 604 may occur near-simultaneously such that the biologic material volume and media are disposed in the reservoir 426 at approximately the same time. In an example where the reservoir 426 is heated, it may be heated to and maintained at a temperature from about 30° C. to about 40° C. prior to block 602, block 604, or after either or both of the biologic material volume and/or media are disposed in the reservoir 426. This heating may be referred to as a preheating, which may take from about 10 minutes to about 45 minutes, or less than 10 minutes depending upon a target temperature or temperature range.

Further in the method 600 at block 606, the biologic material volume disposed at block 602 is completely or partially digested via the enzyme media disposed at block 604. The digestion at block 606 of the biologic material volume disposed at block 602 may occur via heating of the reservoir 426, or via the agitation of the single-walled bowl, or by a combination of both. This digestion may occur over various time periods from 5 minutes to 1 hour, from 15 minutes to 45 minutes, or other periods of time depending upon a type of enzyme(s) used, a number of enzyme(s) used, and/or a volume of each enzyme used at block 604, and the volume of biologic material disposed at block 602. As discussed herein, the agitation of the single-walled bowl causes the paddles 414 to engage with the media and biologic sample and create agitation that promotes and enables digestion. The agitation at block 606 may occur by the partial or complete rotation of the bowl in alternating directions around a central axis, and is not the same as, nor does it generate the force of, the centrifugation discussed herein. The agitation employed to promote digestion at block 606 may comprise whole or partial rotations in different directions around a central axis 124 (FIG. 1), and may occur for a predetermined period of time. The digestion at block 606 may be referred to as a first state of the apparatus, wherein centrifugal forces are not applied and the media and biologic material volume are agitated in the chamber for a predetermined period of time or for a predetermined number of agitation cycles. In one example, the temperature of the reservoir 426 is maintained at about 37° C. during the digestion at block 606, this first state is maintained for a predetermined time period based upon a type of enzyme(s) used, a number of enzyme(s) used, and/or a volume of each enzyme used at block 604, and the volume of biologic material disposed at block 602. The systems discussed herein may comprise a plurality of stored programs comprising parameters for the digestion at block 606 as well as for other states, blocks, and phases discussed herein.

At block 608, in response to and subsequent to the completion of digestion at block 606, centrifugation occurs. As discussed herein, the "completion" of the digestion at block 606 refers to when the digestion has progressed to a point where the cells are still viable but the biologic volume has been broken down such that it is capable of centrifugation at block 608. This centrifugation at block 608 may be characterized by the separation of endothelial cells from the digested volume formed at block 606. In an embodiment, the configuration at block 608 comprises a g-force from 600 G to 1000 G for a time period from about 5 minutes to about 10 minutes. The g-forces or "G" referred to herein is the force of gravity applied to a body, in this case, the force applied to the cells collected in the cell concentration areas which continue to have fluid removed (thus becoming a more concentrated cell volume with the reduced fluid/waste) and remain isolated from the reservoir during at least the centrifugation at block 608.

The centrifugation at block 608 may be referred to as a second state of the cell separation system. The centrifugation at block 608 may comprise programs of various RPM speeds and times for cycles. These cycles may increase in RPM and/or in duration until cessation at block 612 as discussed below. In an embodiment, a single centrifugation cycle may be employed from 500 G to 1000 G for a time period from about 5 minutes to about 10 minutes and in still other examples, multiple centrifugation cycles may be employed that first increase in the G-force applied and then decrease the force applied, leading into the slowed rotation discussed in detail in block 610 below.

In an embodiment, the digestion at block 606 separates a plurality of cells from adipose tissue and fluids, the centrifugation cycle(s) at block 608 acts to force the separation of the cells and the movement of those separated cells into the cell concentration areas 306A and 306B as shown in FIG. 3. In an embodiment, the heating mechanism used to preheat the reservoir 426 during digestion at block 606 is shut off subsequent to block 606 and prior to the initiation of block 608, such that the centrifugation at block 608 may proceed between room temperature (from about 20° C. to about 25° C.) and the temperature employed at block 606. Further at block 608, during separation of the cells into the cell concentration areas 306A and 306B, after a predetermined time period of centrifugation at block 608, clean media may be introduced into the chamber of the single walled bowl via the line 408. This media further displaces a plurality of materials including fat and other tissues and liquids from the reservoir 426 such that those materials are removed from the reservoir 426 as the volume increases via the line 418 that may be coupled to a waste container or other vessel. In some examples, a speed of from 500 G to 800 G may be used at block 608 in order to separate cell volume in the concentration areas 306A and 306B, and in other examples, a speed from 700 G to 900 G may be used for centrifugation at block 608. In some embodiments, at block 608, during centrifugation, a plurality of clean media may be introduced via a fluid line such as 408. The clean media may be added at block 608 to increase the total volume inside the bowl 302 to promote the expulsion of waste, which floats in the media.

Block 610 is a slowed rotation phase and may also be referred to as the third state of the cell separation apparatus. During this phase, which may be from 3 minutes to 45 minutes, a lower centrifugal force, for example, from about 15 G to about 50 G, and in some cases from 20 G to 25 G, is applied at block 610. In one example, at block 610, the rotation of the single-walled bowl is slowed to a predetermined speed or range of speeds, and a temperature of the chamber may be from room temperature to the maximum temperature employed at block 606. The parameters such as speed (force generated) and temperature may be employed at block 610 to enable the separated cell volume to remain in the cell concentration areas 306A and 306B while the remaining fluid from the media and biological volume drains down the interior walls of the chamber.

The waste collected may be removed in whole or in part via the waste outlet 418 or fluid line 416 while the cell volumes are retained in the cell concentration areas 306A and 306B by the centrifugal force applied at block 610. In some examples, a minimum force applied at block 610 may be about 20 G, and a maximum force may be about 50 G. Some waste may remain trapped in 420, where it is isolated from the separated cells. In some examples, the slowed spin of block 610 may be iterative, for example, a first slowed rotation at block 610 may be at 90% of an average speed of block 608, a second, subsequent slowed rotation at block 610 may be at 80% of an average speed of block 608, and subsequent slowed rotations may be at lesser and lesser speeds until a predetermined period has expired or until a predetermined amount of fluid and/or solids has been removed, as determined by volume and/or optic sensors. During block 610, fluid and solids that are small enough to fit through the waste outlet 418 or fluid line 416 are removed and any solids larger than those tubes are retained and isolated by the waste block 420 such that the separated cell volume is not contacted by this material.

At block 612, the rotation is slowed to a stop. The slowing and cessation at block 612 of the rotation causes the cells collected to no longer be compacted in these regions since the force holding the cells in place and concentrating the cell volume (removing liquid) is removed. The normal gravitational force may then be employed to collect cells from the collection areas 306A and 306B to a collection region of the single-walled bowl. Thus, the cells collected in 306A and 306B move from those collection areas to a receptacle. At block 614, the concentrated cells (separated cell volume) may be removed via the clean line 408 via a syringe or other mechanism, this removal is automated and occurs in response to completion of blocks 610 and 612. Blocks 612 and 614 may be collectively referred to as a fourth state of the cell separation apparatus when the bowl is no longer rotating relative to the cradle.

In some examples, at block 616, prior to or simultaneously with the cessation of rotation and removal of cells at blocks 612 and 614, respectively, a wash media is introduced to the chamber. In this example, the introduction of media at block 616 may occur depending upon the rotation speeds, centrifugation programs (cycles), and geometry of the system and collection regions. In an embodiment where wash media is introduced at block 616, the amount employed may be less than 10 mL, 5 mL, or 1 mL, and the wash media is used to ensure that the cells collected in the concentration regions are dislodged and removed at block 616 so that they can be collected at block 614. In this example, block 616 may also be considered as a part of the fourth state of the cell separation apparatus. The blocks discussed in the method 600 are associated with an automated, dynamic method of cell separation and collection, such that the loading of the chamber at blocks 602 and 604 proceeds through the removal and collection at block 612 without manual intervention. In one example, a non-transitory memory stored on a storage device and coupled to the cell separation apparatus comprises a plurality of code executable by a processor. This plurality of code comprises centrifugation programs for samples of varying properties, each program may comprise a flow rate for blocks 602 and/or 604, as well as cell volume and/or concentration targets, flow rates, times, and ranges for forces generated (rotation rate/RPM) at blocks 606, 608, 610, 614, and 616 as appropriate for the actions occurring at each block. Each program may be associated with an overall time to completion from the deposition of the media and biologic material volume to the removal of the separated cells.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

The invention claimed is:

1. A method of using a cell separation system to separate cells, said cell separation system comprising:
    an assembly removably coupled to a containment mechanism, the assembly comprises:
    a single-walled centrifugation bowl comprising a plurality of cell concentration areas, a reservoir, and a center column comprising a plurality of fluid lines,
    a cradle, wherein the cradle comprises a plurality of apertures formed concentrically through the cradle, wherein the centrifugation bowl is removably coupled to the cradle to enable free rotation of the centrifugation bowl while coupled to the cradle, and
    an alignment mechanism coupled to the containment mechanism and the centrifugation bowl to restrict movement of the center column of the centrifugation bowl when the assembly is coupled to the containment mechanism,
    wherein the method comprises:
    (a) agitating, in the reservoir of the cell separation system, a volume of biologic material and a volume digestion media to form a digested volume of biologic material;

(b) centrifuging the digested volume of biologic material in the single-walled centrifugation bowl at a force from about 500 G to about 1000 G from about 5 minutes to about 10 minutes to separate the digested volume into a plurality of concentrated cell volumes and a plurality of waste;

(c) removing a portion of the plurality of waste via at least one fluid outlet;

(d) isolating a different portion of the plurality of waste, wherein the different portion of the plurality of waste comprises waste with a larger diameter than the at least one fluid outlet and is not in contact with the concentrated cell volumes; and (e) removing the concentrated cell volumes from the reservoir.

2. The method of claim 1, wherein step (a) comprises rotating the single-walled centrifugation bowl in each direction around a central axis in an alternating fashion for a predetermined period of time.

3. The method of claim 2, further comprising heating the single-walled centrifugation bowl from about 30° C. to about 40° C.

4. The method of claim 2, further comprising heating the single-walled centrifugation bowl from about 30° C. to about 40° C. during (a).

5. The method of claim 1, wherein (b), (c), (d), and (e) occur from about 20° C. to about 25° C.

6. The method of claim 1, further comprising initiating (a) by execution of a centrifugation program via a processor.

7. The method of claim 6, wherein the centrifugation program is complete subsequent to (e).

8. The method of claim 1, wherein a plurality of centrifugation programs are stored in a non-transitory storage device of the cell separation system.

* * * * *